US005627063A

United States Patent [19]

Divies et al.

[11] Patent Number: 5,627,063
[45] Date of Patent: *May 6, 1997

[54] DEHYDRATED POLYSACCHARIDE GEL CONTAINING MICROORGANISMS AND A HYDROPHILIC SUBSTANCE

[75] Inventors: Charles Divies; Pascal Lenzi, both of Dijon, France; Jacques Beaujeu, Noumea, New Caledonia; Frederic Herault, La Chapelle sur Erdre, France

[73] Assignee: Champagne Moet & Chandon, Epernay, France

[*] Notice: The term of this patent shall not extend beyond the expiration date of Pat. No. 5,389,532.

[21] Appl. No.: 475,059

[22] Filed: Jun. 7, 1995

Related U.S. Application Data

[62] Division of Ser. No. 355,042, Dec. 13, 1994, which is a continuation of Ser. No. 161,681, Nov. 22, 1993, Pat. No. 5,389,532, which is a continuation of Ser. No. 635,531, Feb. 25, 1991, abandoned.

[30] Foreign Application Priority Data

Jul. 7, 1988 [FR] France ................... 88 09249

[51] Int. Cl.$^6$ .................. C12N 11/10; C12N 1/04; C12G 1/00; C12C 11/00
[52] U.S. Cl. ................ 435/178; 426/11; 426/13; 426/15; 435/182; 435/260
[58] Field of Search ................. 435/177, 178, 435/182, 260; 426/11, 13, 15

[56] References Cited

U.S. PATENT DOCUMENTS

| | | |
|---|---|---|
| 1,420,557 | 6/1922 | Klein .................... 435/255 |
| 3,407,072 | 10/1968 | Aizawa et al. .......... 435/255 X |
| 4,246,349 | 1/1981 | Messing et al. ............ 435/176 |
| 4,663,286 | 5/1987 | Tsang et al. .............. 435/178 |
| 5,389,532 | 2/1995 | Divies et al. ............. 435/178 |

FOREIGN PATENT DOCUMENTS 0065376  11/1982  European Pat. Off. .
60-99336  6/1985  Japan .

OTHER PUBLICATIONS

Bashan, Y., Applied and Environmental Microbiology, May 1986, pp. 1089-1098.

Primary Examiner—David M. Naff
Attorney, Agent, or Firm—Bryan Cave LLP

[57] ABSTRACT

A polysaccharide gel enclosing microorganisms is soaked in a solution of a high concentration such as at least 500 g/l of hydrophilic substance and the gel is at least partially dehydrated to provide improved viability of the microorganisms after storage and rehydration of the gel. The dehydration may be carried out in a fluidized bed or by lyophilization. The gel may be in the form of beads or fibers having a double layer structure formed by an internal layer or core of gel containing the microorganisms and an external layer or envelope of gel essentially devoid of the microorganisms. The hydrophilic substance can be a low molecular weight polyol such as glycerol or a sugar such as sucrose, glucose or fructose. The microorganisms in the gel are preferably yeasts and after rehydration the yeast-containing gel is used in the secondary fermentation of wine to produce sparkling wine or champagne.

10 Claims, 4 Drawing Sheets

SORPTION ISOTHERMS OF PARTICLES OF 1.5% ALGINATE GEL SG 1100 (NP) CONTAINING YEASTS

□ BEADS WITHOUT PROTECTIVE SUBSTANCE
○ BEADS CONTAINING 100g SUCROSE/100 ml GEL
● BEADS CONTAINING 100g SORBITOL/100ml GEL

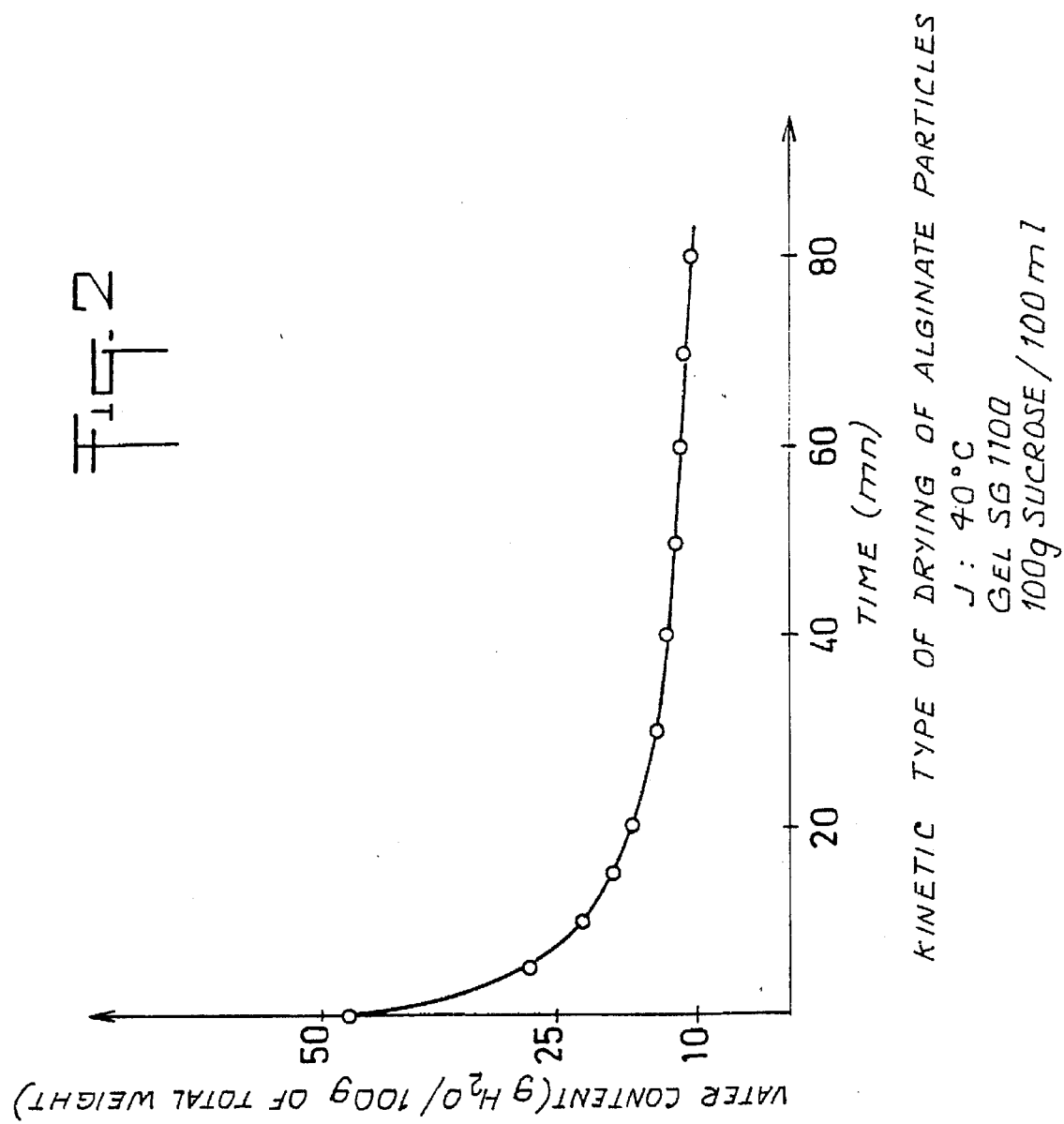

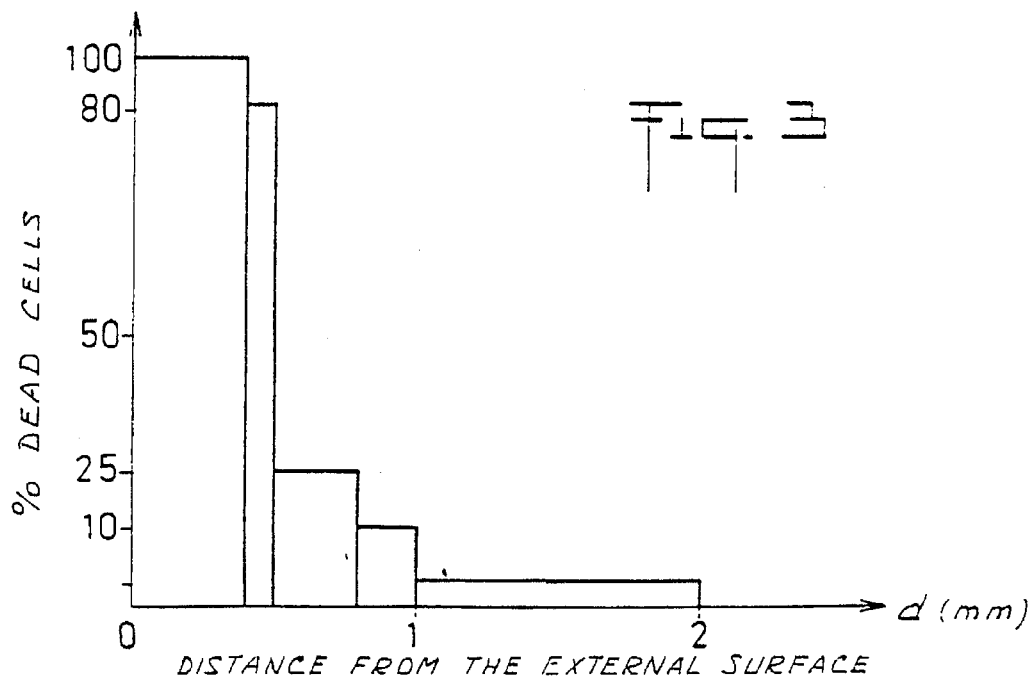
DISTRIBUTION OF DEAD CELLS IN MONOLAYER ALGINATE BEADS AFTER 90 mn OF DRYING AT 40°C.
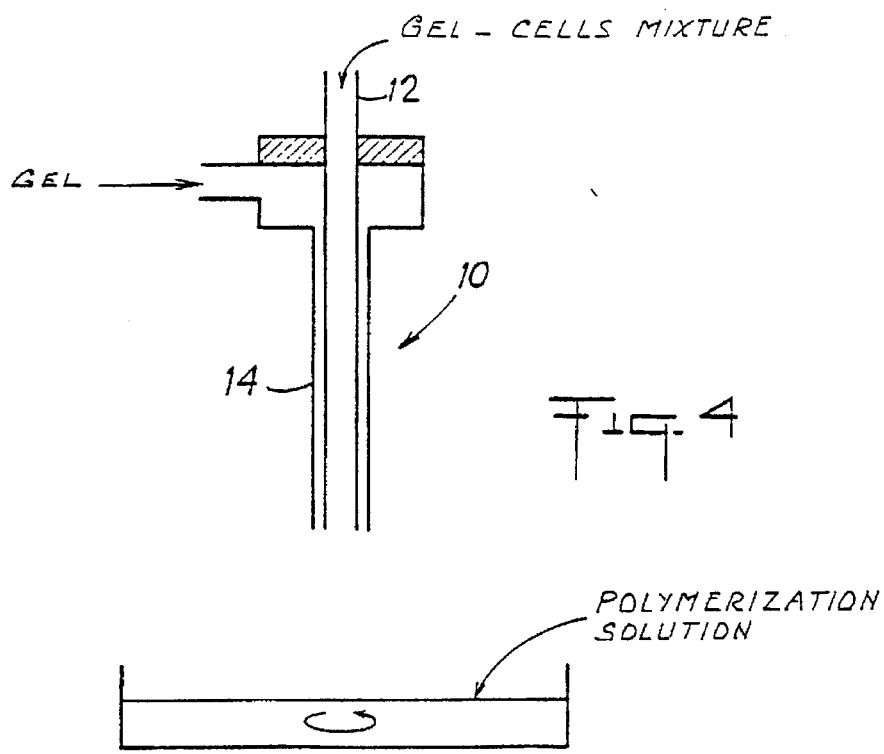

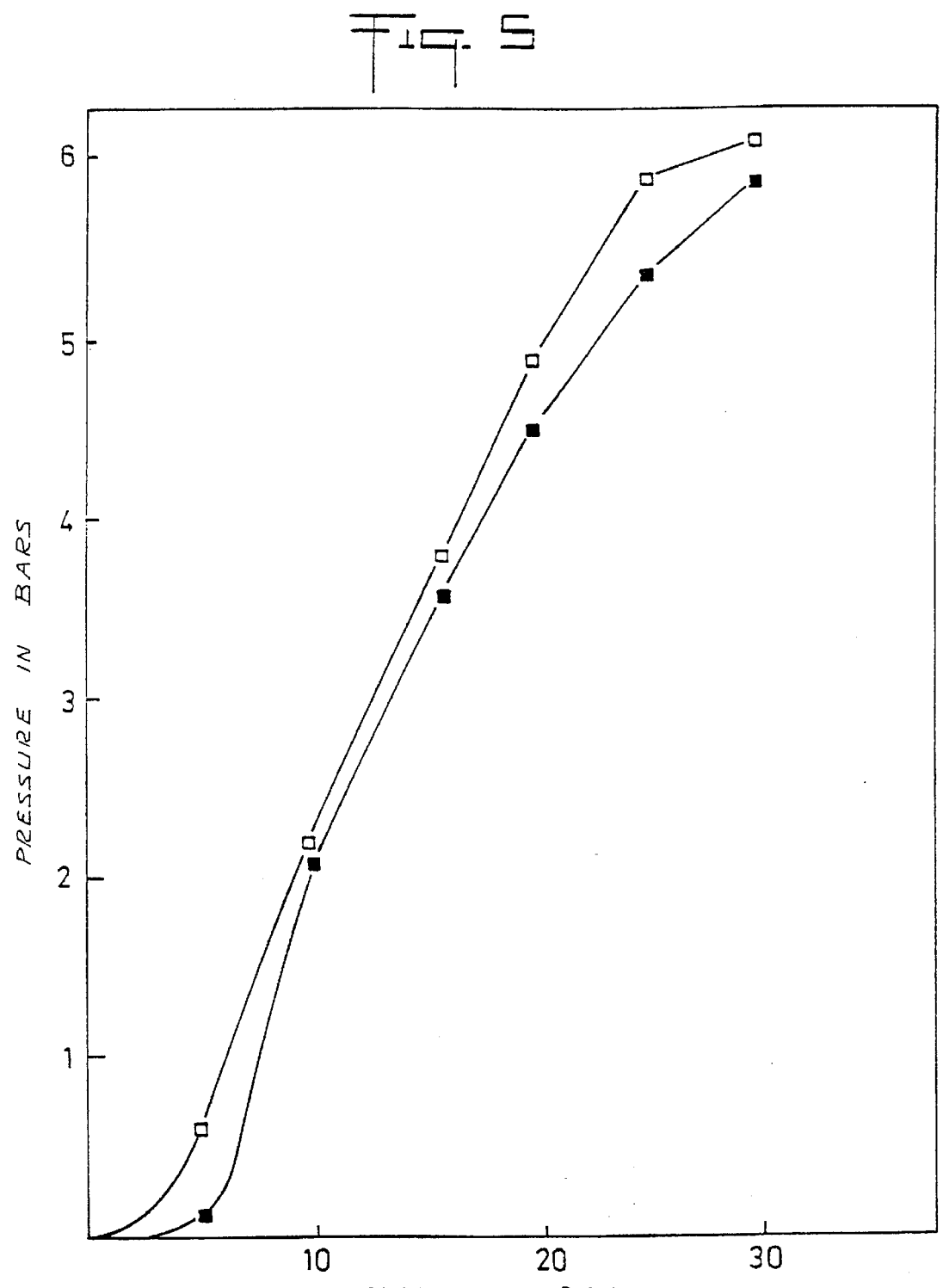

DEHYDRATED POLYSACCHARIDE GEL CONTAINING MICROORGANISMS AND A HYDROPHILIC SUBSTANCE

This is a divisional of U.S. application Ser. No. 08/355,042, filed Dec. 13, 1994, which was a continuation of U.S. application Ser. No. 08/161,681, filed Nov. 22, 1993, now U.S. Pat. No. 5,389,532 granted Feb. 14, 1995, which was a continuation of U.S. application Ser. No. 07/635,531, filed Feb. 25, 1991, now abandoned.

BACKGROUND OF THE INVENTION

1. Field of the Invention

The present invention relates essentially to a process for the preparation of micro-organisms enclosed in appreciably dehydrated gels, gels obtained and their use for the preparation of fermented drinks.

2. Description of the Related Art

In the state of the prior art, it is known that immobilized micro-organisms can be used in the production of fermented drinks such as wine and beer (FR-A-2 320 349 and FR-A-2 359 202). Their use has also been suggested for classical champagnization (FR-A-2 432 045) as well as for the manufacture of sparkling drinks with a variable degree of alcohol (FR-A-2 601 687). These publications, as well as others (in particular JP-A-57-150 385 or EP-A-173 915) have emphasized the performances of reactors with immobilized cells.

These techniques have made possible the carrying out of fermentations with mixtures of micro-organisms of different categories (mixture of lactic acid bacteria and mixture of yeast).

However, the implementation of the process on an industrial scale came up against the difficulty of having available particles capable of being preserved for a long period.

Micro-organisms in the enclosed form may be used without an appreciable drop of activity over long periods when the nutrition of the micro-organisms concerned is respected.

It has been possible to note a toxicity of the products of fermentation which leads to a partial ageing of the cells (article by DIVIES et al. in Annales de microbiologic, 1977, pages 349–358).

It was thus preferred in this particular case to use a battery of reactors of defined life time and to carry out the partial renewal of the microbial particles in a programmed manner.

Problems of mechanical resistance of the gel have also managed to arise and are described in JP-A-57-150 385.

It thus appears crucial at the industrial level to plan the elaboration of the particles for inclusion of the micro-organisms and to centralize the production of them. It is also necessary to bring about the inclusion of the micro-organisms in the gels which ensures them excellent viability over a period of time.

Now, it became apparent that the micro-organisms enclosed in gels were very sensitive and tolerated storage for a prolonged period of time with difficulty.

In order to overcome this disadvantage of storage, storage processes including a drying have already been suggested.

The commercial preparations of micro-organisms enclosed in dried gels naturally need to be capable of rehydration and maintain excellent viability after rehydration.

Certain solutions have been proposed which permit storage over periods which may attain 6 months to 1 year in a protective packing at a relatively low temperature of 4° to 10° C. (see BEKER and RAPOPORT in Advances in Biochemical Engineering and Biotechnology, Volume 35, 1987, pages 128 to 171). This publication discloses it is conventional to add wetting agents such as esters of sorbitol, glycerol or propylene glycol, fatty acids or other compounds, in an amount of 0.5–5% of the dry weight of the yeast being dried, prior to dehydration.

The TATE document EP-A-0 065 376 describes a process for the preparation of enzymes immobilized in a gel which is then dried if appropriate and, after drying, is placed in contact with glycerol (page 10, 2nd paragraph and claim 3). A placing in contact after drying does not make it possible to preserve the structure of the gel which renders its rehydration difficult, a problem which is resolved by the present invention which will be described below.

The document FR-A-2 519 022 describes a process for the preparation of inocula with long viability and having an improved resistance to temperature which comprises a drying of the micro-organisms in accordance with various drying processes. This document also describes in its introduction many documents of the prior art relating to drying of gels enclosing micro-organisms.

According to this document FR-A-2 519 022, at the start a culture of micro-organisms is grown in a standard culture medium for several days.

To this culture medium, a gellable polymer, which may be a polysaccharide, xanthan or an alginate, may be added.

After gelation which enables the inclusion of a micro-organism in the culture medium to be carried out, drying is undertaken until an activity of water in the inoculum is produced below its critical value to a value lower than 0.5, this value being maintained during storage (see claim 1, in particular). Preferably, the activity of water in the inoculum is maintained below 0.3 and preferably even below 0.1 (claim 2).

It is to be noted that according to this document attention is not paid to the special problem of the rehydration of the dry or appreciably dehydrated gel so as to obtain rehydrated gels having a structure approximately identical with that which they possessed before their dehydration.

Now, experient has shown that the dehydrated or dried particles obtained by the procedure described in this document rehydrate with very great difficulty. In the best cases, in the presence of culture medium, the rehydration remains limited at 20% humidity, the particles always remaining very small, dried up, ungraded with respect to size and very hard.

If a supplementation with hydrophilic substances such as carrageenin or carob seed grain is carried out, this causes the gel to become brittle without improving the rehydration of the gelled polymer, and this is particularly true in the case of the employment of an alginate. In the best cases, viabilities incompatible by some few percent with an industrial use may be obtained.

Hence, it appears necessary to dispose of easily rehydratable gels containing a maximum of viable micro-organisms after rehydration, and to do so even after a long period of storage.

SUMMARY OF THE INVENTION

Hence, the aim of the present invention is to resolve the new technical problem consisting of the provision of a solution making it possible to dispose of dried or essentially dehydrated gels, easily rehydratable, containing a maximum of viable micro-organisms after rehydration, and to do this even after a prolonged period of storage.

Another aim of the present invention is to resolve the new technical problem consisting in the provision of a solution making it possible to dispose of gels containing a maximum of viable micro-organisms after rehydration, preserving an essentially unchanged structure of the gel after rehydration, maintaining a good stability of this gel compatible with an industrial use of the rehydrated gel.

These technical problems are resolved simultaneously for the first time by the present invention in an extremely simple manner which can be used on an industrial scale.

Thus, according to a first feature, the present invention provides a procedure for the preparation of micro-organisms enclosed in at least partially dehydrated gels exhibiting improved viability after rehydration, comprising:

a) the inclusion of micro-organisms in a polymer solution capable of being transformed into a gel;

b) the gelation of this solution containing the microorganisms so as to form a gel enclosing the microorganisms; and c) the drying of this gel enclosing the micro-organisms in order to obtain an at least partially dehydrated gel, characterized in that gels enclosing the micro-organisms having a high concentration of hydrophilic substances are prepared which are then subjected to the said drying step.

By "high concentration" is meant a concentration of hydrophilic substances markedly higher than the concentration of this substance usually used as protective drying agent. Preferably, this concentration of hydrophilic substances is at least twice the usual concentration, even better at least five times the usual concentration.

According to another advantageous characteristic of the process according to the invention, the above-mentioned hydrophilic substance is one of low molecular weight. This hydrophilic substance is preferably selected from among polyols such as sorbitol, inositol, glycerol; the sugars such as sucrose, glucose, fructose. Sucrose constitutes the sugar particularly preferred because it enables particularly unexpected results to be obtained.

According to a particularly advantageous embodiment of the process according to the invention, the concentration of sucrose is at least equal to 500 g/l, and preferably about 1000 g/l of the polymer solution capable of being transformed into a gel.

According to another advantageous characteristic of the process according to the invention, a culture of cells of micro-organisms is grown until the stationary phase is attained, which corresponds in particular in the case of yeasts to a low degree of budding or the initiation of division. Preferably, this low degree of budding is lower than 5%. This makes it possible to unexpectedly increase the viability of the micro-organisms, particularly in the case of the yeasts.

In accordance with another advantageous characteristic of the process according to the invention, a gel is prepared having a double layer structure comprising an internal layer or core of gel containing the cells of the micro-organisms and an external layer or envelope of gel practically devoid of micro-organisms. This gel may exhibit the form either of beads, or fibres, as is well known in the techniques of gelation.

In order to produce a gel having a double layer structure, the previously known processes may be used, such as those described for example in the document JP-A-57-150 385 by preferably using the process described in this document which consists of forming the external layer or envelope with a gellable solution. It is also possible to use the technique described in the document GB-A-1 158 662 or U.S. Pat. No. 4,386,895 or U.S. Pat. No. 3,396,116, or also EP-A-0 140 336 or U.S. Pat. No. 3,015,128 or U.S. Pat. No. 3,310,612 or also the techniques of inclusion preparations described in an article by P. G. Krouvel in Biotechnology and bioengineering (1980), volume 22, page 681 or the document Microcapsules Processing and Technology (Asaji Kondo) 1979, pages 62 to 66.

In accordance with a particularly advantageous characteristic of the process according to the invention, the thickness of the external layer or envelope, in the case of beads having a diameter of about 4 mm, is less than 0.8 mm.

According to another advantageous characteristic of the process according to the invention, the above-mentioned high concentration of hydrophilic substances in the gel is obtained by soaking the gel in a solution of hydrophilic substances having the said high concentration up to equilibrium, then by subjecting the gel to the above-mentioned drying step.

In accordance with another advantageous characteristic of the process according to the invention, a drying of the gel enclosing the microorganisms having the above-mentioned high concentration of hydrophilic substances is carried out until an activity of water lower than about 0.5 is obtained.

In accordance with another advantageous characteristic of the process according to the invention, the above-mentioned drying is carried out at a temperature close to 40° C. and preferably the temperature is increased to attain about 50° C. by the end of drying.

In accordance with another advantageous characteristic of the process according to the invention, the above-mentioned drying of the gel enclosing the micro-organisms, containing a high concentration of hydrophilic substances, is carried out in a fluidized bed.

In accordance with another characteristic of the process according to the invention, a drying of the gel containing the micro-organisms containing the above-mentioned high concentration of hydrophilic substances is carried out by means of a lyophilization technique in a vacuum, the temperature of lyophilization is preferably of the order of about −80° C.±10° C.

In accordance with another advantageous characteristic of the process according to the invention, the gel containing the micro-organisms containing the above-mentioned high concentration of hydrophilic substances is preserved at least partially dehydrated in a water vapour-tight packing which is preferably maintained at a relatively low temperature, preferably at about 4° C.

In accordance with a preferred characteristic, this storage takes place in a controlled atmosphere very poor in oxygen and enriched in $CO_2$.

In accordance with another advantageous characteristic of the process, according to the invention, the micro-organisms are yeasts, in particular of the genus Saccharomyces and Schizosaccharomyces.

In accordance with a second feature, the present invention also relates to the use of the gels enclosing at least partially dehydrated micro-organisms mentioned above for the preparation of fermented or refermented drinks as well as for the preparation of ethyl alcohol.

The present invention also relates to the gels including the micro-organisms having the above-mentioned high concentration of hydrophilic substances as a novel product, where appropriate in a rehydrated state.

The invention makes it possible to achieve the previously mentioned non-evident, unexpected technical results by resolving the new technical problems previously set out by discovering in an unexpected manner that it was possible to preserve both of the structure of the gels and the viability of the micro-organisms if a high concentration of hydrophilic substances was used. As has been mentioned previously, these hydrophilic substances are preferably selected from among the polyols such as sorbitol, inositol, glycerol; the sugars, in particular sucrose, glucose, fructose; the sugar presently much preferred is sucrose. The high concentration of sucrose is preferably at least 500 g/l, and more preferably about 1000 g/l of the polymer solution capable of being transformed into a gel.

In this way, at least partially dehydrated Eels are obtained which can easily be rehydrated even after a prolonged period of storage.

The general conditions of the process for the preparation of the at least partially dehydrated gels including the micro-organisms are the following:

a) a culture of the micro-organisms is first grown in a suitable culture medium containing a carbon source, in particular carbohydrates, until the stationary phase is obtained, which corresponds in particular in the case of the yeasts to a low degree of budding or cell division, which is preferably lower than 5%.

b) An inclusion of the micro-organisms present in the culture medium in an easily gellable or solidifiable polymer is carried out, as is standard.

This inclusion may be done by the standard technique of droplet formation so as to produce beads of gel enclosing the micro-organisms.

Preferably, according to the invention, an inclusion with a double layer is carried out so as to produce a protective external layer or envelope of gel practically free of cells of micro-organisms.

c) The gel thus formed, in particular in the form of beads or fibres, is soaked in a solution containing a high concentration of hydrophilic substances, such as previously defined, preferably constituted by a sugar.

In the case of the employment of sucrose, the concentration of hydrophilic substances is preferably at least equal to 500 g/l, even better about 1000 g/l of the polymer solution.

This soaking is carried out until an equilibrium between the solution and the gel is obtained.

d) The drying of the thus soaked gel is then undertaken, after separation of the latter from the solution containing the above-mentioned hydrophilic substances by using any previously known suitable drying treatment.

It is possible to use, for example, the technique of the fluidized bed, lyophilization or even a desiccator containing a desiccant.

e) It is then possible to store the at least partially dehydrated gel enclosing a micro-organism under an atmosphere enriched in $CO_2$.

f) The particles can then be rehydrated according to the methodology usually used in the case of the dried yeasts already on the market for the purpose of using them.

Other aims, characteristics and advantages of the invention will become clearly apparent in the light of the explanatory description which follows made with reference to examples of the embodiment below in correlation with the appended figures. These examples are naturally given only as illustrations of the invention and hence should in no way be interpreted as constituting a limitation of the scope of the invention. In the present description and the examples, all of the percentages are given by weight, except where indicated otherwise.

BRIEF DESCRIPTION OF THE DRAWINGS

In the accompanying drawings:

FIG. 2 is a graph showing the kinetic drying curve of gel beads prepared by the process of the invention;

FIG. 3 is a schematic illustration of the spatial distribution of dead microorganism cells in gel beads prepared in accordance with one embodiment of the invention;

FIG. 4 is a schematic illustration of a device for preparing double layer microorganism-containing gel beads in accordance with a second, preferred embodiment of the invention; and FIG. 5 is a graph illustrating comparative pressure changes which occur during the re-fermentation in closed vessels of a wine product utilizing microorganism-containing gel beads which have been prepared with and without the preferred drying technique of the invention.

DESCRIPTION OF THE PREFERRED EMBODIMENT

EXAMPLE I

Figure 1:
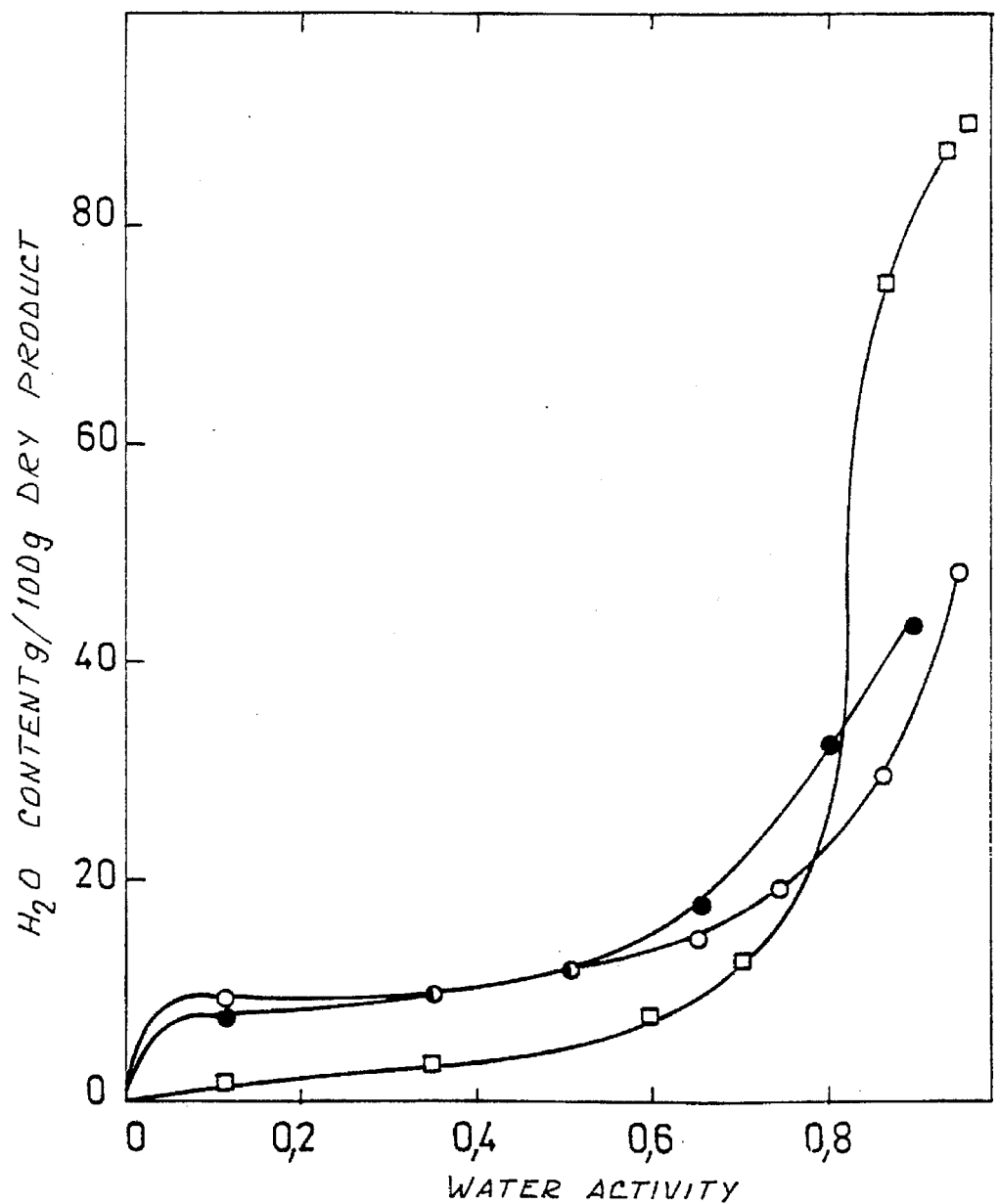
FIG. 1 is a graph of the comparative sorption isotherms of microorganism-containing gel-beads prepared with and without the protective hydrophilic substances employed in accordance with the invention.

Preparation of at Least Partially Dehydrated Gel According to the Invention by Using as Microorganism a Strain of *Saccharomyces cerevisiae*

In this example, a strain of *Saccharomyces cerevisiae* is used as strain of micro-organisms.

A Malt Wickerham with 10 g/l glucose as hydrocarbon source is used as culture medium.

The yeasts are cultivated in Erlenmeyers on a shaking platform at 28° C. and harvesting is done after 32 h of culture at a star, at which the micro-organisms have a low degree of budding, preferably not exceeding 5%, and a content of the reserve substances glycogen and trehalose here 15 and 8%, respectively, by determination according to the techniques described by HERBERT et al. in Methods in Microbiology, Volume 5B, 1971, pages 210 to 344.

In accordance with a variant, it is possible to obtain under the same culture conditions higher amounts of reserve substances, for example about 22% of glycogen and about 13% of trehalose by using the modified Malt Wickerham.

The culture medium is centrifuged so as to separate the micro-organisms which are placed in suspension in an aqueous solution. This latter is then mixed with an aqueous solution of sodium alginate "CECA SG 1100" so as to obtain a final solution of 1.5%.

The mixture is then pumped and dripped into a solution of 0.2M $CaCl_2$ at pH=7.

After 45 min of contact, the hardened particles, available in the form of beads of calcium alginate enclosing the cells of micro-organisms, are rinsed with distilled water and exhibit a mean diameter of 2.7 mm. These beads contain about $5.10^8$ cells of micro-organisms/ml of beads if these preparations are destined for a process of secondary fermentation according to the Champagne technique, or $2.10^8$ cells/ml of beads in the case of processes of alcoholic fermentation (reaction in closed vessels or batches for preparation of fermented drinks or production of ethanol).

In accordance with an essential characteristic of the process according to the invention, after formation of the beads enclosing the micro-organisms they are soaked in a solution containing a high concentration of hydrophilic substances of low molecular weight, for example, a solution of sucrose having a concentration of 100 g/100 ml. This immersion of the beads in this sucrose solution is maintained until an equilibrium is obtained so as to give rise to a final concentration of sucrose in the beads equal to about 100 g/100 ml of gel.

Other sugars such as glucose or fructose may also be used instead of sucrose. It is also possible to use hydrophilic substances exhibiting a vitreous structure after dehydration such as sorbitol, glycerol, inositol.

The particles thus impregnated are drained then introduced into a dryer with a fluidized bed, for example of the RETSCH type available from Bioblock Scientifics, presented in the 1988 catalogue on page 152, with programmable air fluxes and temperatures between 900–1800 l/min and 40°–120° C., respectively.

The desorption isotherms of the beads without the protective hydrophilic substances according to the invention, and containing sucrose and sorbitol at a concentration of 100 g/100 ml as protective hydrophilic substances according to the invention are shown in FIG. 1.

The equilibrium of the beads is obtained by desorption under different atmospheres controlled by saturated solutions at 25° C.

In FIG. 2, the drying curve produced at 40° C. by using ambient air (relative humidity close to 65%) has been plotted.

In accordance with an advantageous characteristic, an activity of water $a_w$ equal to about 0.2 is attained by using drier air and also a higher drying temperature. Experiment has shown that the cells of micro-organisms preserve their viability if the temperature is increased to about 50° C. at the end of dehydration.

The viabilities observed as a result of the two dehydration treatments by fluidized bed leading to an activity of water included between 0.3 ad 0.4 are reported in Table 1 below.

TABLE 1

% of viabilities observed during two drying treatments at 40° C. as a function of the state of the culture

| Phase of the culture | Harvest | Before drying | After drying |
| --- | --- | --- | --- |
| Beginning of stationary phase 25% buds | 99 | 99 | 25 |
| 32 h of culture 3% buds | 99 | 99 | 90 |

The measurements of viability were carried out after rehydration of the beads or particles in a 24 g/l sucrose solution (which is close to the composition of wine) for 1 h at room temperature (25° C.) in a shaken medium.

The beads which were translucent at the beginning become opaque again after rehydration.

After rehydration the final water content is identical with the initial water content.

Redissolution of the beads is effected by the use of a sterile solution of glucose and sodium citrate having the following composition:

| | |
| --- | --- |
| Pancreatic peptone | 1.2 g |
| Glucose | 10 g |
| NaCl | 10 g |
| Trisodium citrate | 20 g |
| Distilled water as required | 1000 ml |

It is observed that the yeasts obtained exhibit a remarkable stability in sealed containers at room temperature since a viability of 86% is obtained after 15 days of storage and after 2 months the viability remains higher than 50%.

Furthermore, it is to be noted that a lowering of the storage temperature to 4° C. makes it possible to maintain a viability higher than 90% after the same period of storage.

The use in a storage atmosphere based essentially on $CO_2$ at room temperature also improves survival since after 17 days of storage micro-organisms, in this case yeasts, are obtained exhibiting 94% of activity.

Re-introductions into the wine base in the process are quite satisfactory.

A pressure change curve realised with the aid of dried or dehydrated beads according to the invention includes yeasts which were cultivated until a level of glycogen of about 20% in conformity with this example had been obtained, in comparison with control beads prepared with the same yeasts and not subjected to a drying, is illustrated in FIG. 5.

It is possible to observe from the curve of pressure changes during the course of the process of secondary fermentation that the beads obtained according to the invention after drying in conformity with the process according to the invention and rehydration have a behaviour essentially similar to control beads not subjected to such a drying.

EXAMPLE II

Preparation of Double Layer Gel

It has been possible to observe that the preparation of the micro-organisms enclosed, for example, in beads according to Example I, results in very good survival.

Nonetheless, additional researches have made it possible to establish that the dead micro-organisms were not distributed uniformly in the sphere of the gel, preferably of alginate.

The technique of dissolution previously described makes it possible to demonstrate this distribution.

The scheme of the spatial distribution of the dead cells in the particles of Example I, which are monolayers, from the external surface of the particles, is represented in FIG. 3.

91% of the dead cells are distributed in the first 400 microns of a sphere 4 mm in diameter.

The experiments carried out by the inventors have made it possible to demonstrate that it is possible to improve the survival of the micro-organisms appreciably if double layer gels are prepared, i.e. comprising an internal layer or core enclosing the cells of micro-organisms and an external layer or envelope of protection practically devoid of cells of micro-organisms. The corresponding technique for the preparation of the double layer gel, in particular in the form of beads, is known in the literature presented at the beginning of the description, in particular from GB-1 158 662 or the document Microcapsules Processing and Technology (Asaji Kondo) 1979, page 62.

For a better understanding, the outline of the principle of a conduit with two concentric tubes is shown in FIG. 4 as a reminder. This conduit 10 comprises a central axial tube 12 into which the mixture of a gel solution, for example a gel of sodium alginate, containing the cells of micro-organisms in suspension is introduced.

In the external tube 14, concentric with the internal tube 12, the gel solution is introduced alone, for example sodium alginate devoid of cells of micro-organisms so as to form double layer drops in a known manner.

It is preferable according to the invention that the external layer forming the protective envelope has a thickness of about 0.35 to 0.70 mm for a diameter of about 4 mm for the beads or droplets.

As a result of this double layer structure, one is thus led to avoid killing the cells of micro-organisms during the drying carried out as previously described.

EXAMPLE III

Preparation of Gel Enclosing *Saccharomyces uvarum*

The procedure indicated in Example I is used except that brewery strain, *Saccharomyces uvarum*, is employed as strain of micro-organisms.

The same results are obtained with a viability higher than 90%.

The re-introductions into the worts of beer of 12.5% degree Plato and 80% of target fermented sugars are quite satisfactory.

EXAMPLE IV

Preparation of Gel Enclosing Schizosaccharomyces

The procedure indicated in Example I is used, except that a standard strain of Schizosaccharomyces is employed as micro-organisms. This strain is reputed for giving very poor survivals under the conditions of standard dehydration.

Nonetheless, according to the invention, in a totally unexpected manner, results comparable to other strains are obtained with a viability higher than 90% after drying and rehydration.

EXAMPLE V

Preparation of Gel enclosing Cells of *Saccharomyces cerevisiae* by Means of Dehydration in a Controlled Atmosphere Beads are prepared as in Example I.

The beads are placed in water-tight twist-off containers (750 ml), the humidity of the air of which is controlled by saturated salt solutions or solutions of glycerol.

The activity of the water is checked by refractometry in the case of the glycerol solutions or by means of the NOVASINA EJ 3 apparatus in the case of the salt solutions.

The equilibrium of the beads is obtained by desorption. After 250 to 300 h of being placed in equilibrium, the viability is measured as previously described.

The results obtained are usually worse than those obtained by a more rapid drying in a fluidized bed.

The best degrees of preservation are obtained with an activity of water less than 0.5.

At an activity of 0.8 or more, the survival of the micro-organisms is lower than 5% whereas at an activity of 0.11 it is higher than 40%.

EXAMPLE VI

Preparation of Gel Enclosing Cells of *Saccharomyes cerevisiae* by Means of Lyophilization The preparation of the beads is identical with that of Example I preferably using sucrose as the protective hydrophilic substance at the same concentration.

Under the operating conditions, a freezing temperature of $-30°$ C. leads to a less good preservation of the structures of the particles than a temperature of $-75°$ C. to $-80°$ C. with a more rapid rate of cooling.

The frozen particles are placed in a USIFROID SMJ lyophilizer.

The sublimation is conducted under a high vacuum (<0.025 mmHg), the reheating is carried out in stages at $-40°$ C., $0°$ C. and $20°$ C.

The complete cycle takes 24 h to result in an activity of water of 0.4.

The survival levels of the cells of micro-organisms obtained are always higher than 80%.

The conditions of rehydration are identical with those used in Example I.

We claim:

1. An at least partially dehydrated gel containing viable microorganisms and a sugar, which has been obtained by a process comprising:
    (a) dispersing the microorganisms in a gellable polysaccharide solution;
    (b) gelling the polysaccharide solution containing the microorganisms to form a gel enclosing the microorganisms;
    (c) soaking the gel enclosing the microorganisms in a solution containing a sugar selected from the group consisting of sucrose, glucose and fructose in an amount of at least 500 g/l of the solution and for a period of time sufficient to reach equilibrium;
    (d) separating the equilibrated gel containing the microorganisms from the solution and recovering the gel; and
    (e) drying the gel to obtain an at least partially dehydrated gel.

2. The gel of claim 1, wherein, prior to step (a), a culture of cells of the microorganisms is grown until a stationary growing phase is reached.

3. The gel of claim 1, wherein the gel is in the form of beads or fibers, each of which has a double layer structure comprising an internal layer or core of gel containing the cells of the microorganisms and an external layer or envelope of gel essentially devoid of the microorganisms.

4. The gel of claim 1, wherein the gel is in the form of beads, each of which has a diameter of about 4 mm, and wherein the thickness of the external layer or envelope is less than 0.8 mm.

5. The gel of claim 1, wherein the gel has a water activity less than 0.5.

6. The gel of claim 1, wherein said at least partially dehydrated gel is stored in a water vapor-tight packet maintained at a temperature of about $4°$ C.

7. The gel of claim 1, wherein said partially dehydrated gel is stored in a controlled atmosphere, which is low in oxygen content and is enriched in $CO_2$.

8. The gel of claim 1, wherein the gel is dried in step (e) in a fluidized bed.

9. The gel of claim 1, wherein the gel is dried in step (e) by lyophilization under vacuum.

10. The gel of claim 1, wherein the lyophilization is performed at a lyophilization temperature of $-80°$ C.$\pm 10°$ C.

* * * * *